United States Patent
Kim et al.

(10) Patent No.: US 9,717,769 B2
(45) Date of Patent: Aug. 1, 2017

(54) METHOD FOR PROTECTING KIDNEY FUNCTION

(71) Applicant: FUGENBIOPHARMA CO., LTD., Seoul (KR)

(72) Inventors: Yoon Soo Kim, Seongnam-si (KR); Hye Dong Yoo, Seoul (KR); Eun Ji Shin, Seoul (KR)

(73) Assignee: FUGENBIOPHARMA CO., LTD., Seoul (KR)

( * ) Notice: Subject to any disclaimer, the term of this patent is extended or adjusted under 35 U.S.C. 154(b) by 0 days.

(21) Appl. No.: 15/361,145

(22) Filed: Nov. 25, 2016

(65) Prior Publication Data

US 2017/0151294 A1 Jun. 1, 2017

(30) Foreign Application Priority Data

Nov. 26, 2015 (KR) .......................... 10-2015-0166515

(51) Int. Cl.
| | | |
|---|---|---|
| *A61K 36/07* | (2006.01) | |
| *A61K 31/715* | (2006.01) | |
| *A61K 9/19* | (2006.01) | |
| *A61K 33/24* | (2006.01) | |

(52) U.S. Cl.
CPC ............ *A61K 36/07* (2013.01); *A61K 9/19* (2013.01); *A61K 31/715* (2013.01); *A61K 33/24* (2013.01); *A61K 2236/30* (2013.01); *A61K 2236/51* (2013.01)

(58) Field of Classification Search
None
See application file for complete search history.

(56) References Cited

U.S. PATENT DOCUMENTS

2014/0193454 A1* 7/2014 Kim ................. A61K 36/07
424/195.15

\* cited by examiner

*Primary Examiner* — Kristin Vajda
(74) *Attorney, Agent, or Firm* — Sughrue Mion, PLLC

(57) ABSTRACT

The present invention relates to a method for protecting a kidney, which comprises administering an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, in an effective amount, to a subject in need of protecting a kidney. The method is effective in protecting a kidney from renal toxicity caused by an anti-cancer agent.

16 Claims, 1 Drawing Sheet

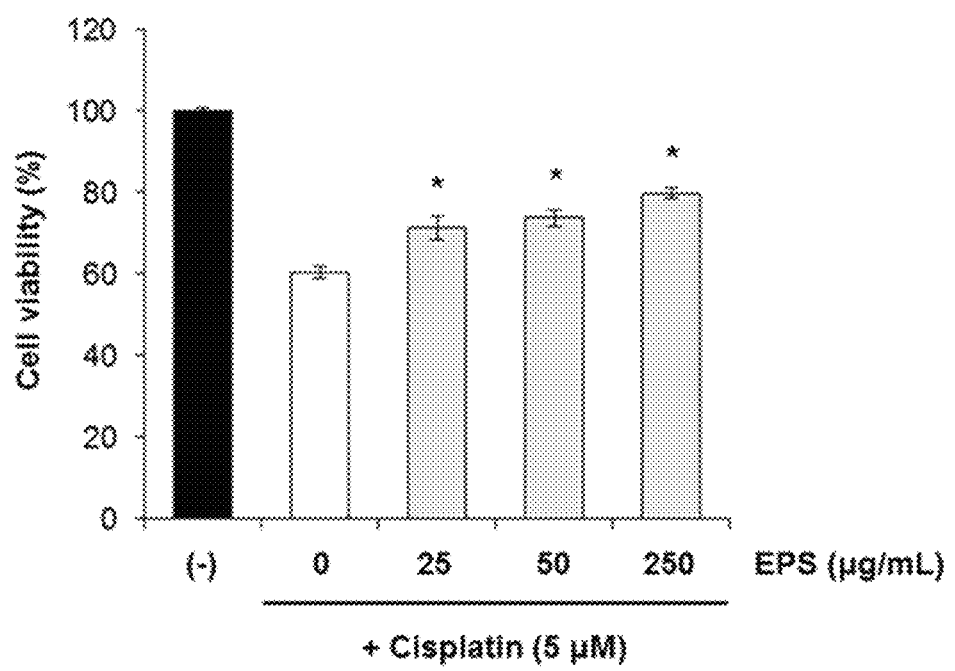

METHOD FOR PROTECTING KIDNEY FUNCTION

TECHNICAL FIELD

The present invention relates to a method for protecting kidney function, and more particularly, it relates to a method for protecting a kidney by administering an active ingredient produced by *Ceriporia lacerata*; a mycelial culture medium of *Ceriporia lacerata* containing the active ingredient; a dried powder of the mycelial culture medium; or an extract of the mycelial culture medium, as an effective ingredient.

BACKGROUND ART

Anti-cancer agents are used as medication therapy for cancer patients. However, such anti-cancer agents are toxic to normal tissues as well as cancer tissues, limiting the application thereof.

Cisplation (or cis-diammine-dichloroplatinum [II]), an exemplary anti-cancer agent, is widely used in clinical practice as a chemotherapeutic agent for the treatment of ovarian cancer, bladder cancer, lung cancer, head and neck cancer, testicular cancer, and the like (Rosenberg B., *Cancer*, 55:2303-2315, 1985). Cisplatin is known to attack cancer cells by producing active oxygen species, and exhibit anti-cancer effects by inducing inter-intrastrand cross-linking of DNA and the DNA adduct formation in cancer cells. However, it has been reported that adverse events such as hearing loss, neurotoxicity, and renal toxicity arise if the dose of the drug exceeds a pre-determined limit during treatment, and also hepatic toxicity is frequently observed when high concentration cisplatin is administered. These adverse events by cisplatin are closely related to the increased lipid peroxidation due to active oxygen species produced by cisplatin, inhibition of the antioxidation enzyme activity present in the tissue, depletion of glutathione, and collapse of intracellular calcium homeostasis.

Recently, it has been observed that cisplatin-induced renal toxicity is effectively inhibited if cisplatin and glutathione ester are administered together (Babu E. et al., *Mol. Cell Biochem.*, 144: 7-11, 1995), and much interest is drawn to inhibiting the toxicity of cisplatin by ingestion of antioxidants in diet.

Meanwhile, *Ceriporia lacerata* is a kind of white-rotting fungus and known to conduct co-metabolism, i.e., lignin decomposition, in order to use carbon sources such as cellulose, hemi-cellulose, other polysaccharides, and glycerol, etc., in the ecosystem.

Regarding the medicinal use of *Ceriporia lacerata* or an extract thereof, only the use for diabetic treatment of the extract of the culture medium of *Ceriporia lacerata* is known by Korean Patent No. 10-1031605 filed by the present inventors, and there has been no report on the use of *Ceriporia lacerata* for protecting a kidney.

DISCLOSURE OF INVENTION

Technical Problem

The present inventors have found that an active ingredient produced by *Ceriporia lacerata*; a mycelial culture medium of *Ceriporia lacerata* containing the active ingredient; a dried powder of the mycelial culture medium; or an extract of the mycelial culture medium shows a kidney-protection effect from renal toxicity caused by an anti-cancer agent.

It is one object of the present invention to provide a method for protecting a kidney comprising administering an active ingredient produced by *Ceriporia lacerata* to a subject in need thereof.

Solution to Problem

In accordance with one object of the present invention, there is provided a method for protecting a kidney, which comprises administering an extracellular polysaccharide produced by *Ceriporia lacerata*; a mycelial culture medium of *Ceriporia lacerata* containing the extracellular polysaccharide; a dried powder of the mycelial culture medium; or an extract of the mycelial culture medium, in an effective amount, to a subject in need of protecting a kidney.

In accordance with another object of the present invention, there is provided a method for protecting a kidney, which comprises administering a composition containing an extracellular polysaccharide produced by *Ceriporia lacerata*; a mycelial culture medium of *Ceriporia lacerata* containing the extracellular polysaccharide; a dried powder of the mycelial culture medium; or an extract of the mycelial culture medium, as an effective ingredient, to a subject in need of protecting a kidney.

In accordance with another object of the present invention, there is provided a method for protecting a kidney, which comprises administering a composition consisting essentially of an extracellular polysaccharide produced by *Ceriporia lacerata*; a mycelial culture medium of *Ceriporia lacerata* containing the extracellular polysaccharide; a dried powder of the mycelial culture medium; or an extract of the mycelial culture medium to a subject in need of protecting a kidney.

In accordance with one embodiment of the present invention, the subject in need of protecting a kidney may be a patient whose kidney is damaged by anti-cancer therapy. More particularly, the anti-cancer therapy may be anti-cancer agent therapy.

Advantageous Effects of Invention

An extracellular polysaccharide (also known as exopolysacchareide) produced by *Ceriporia lacerata*; a mycelial culture medium of *Ceriporia lacerata* containing the extracellular polysaccharide; a dried powder of the mycelial culture medium; or an extract of the mycelial culture medium according to the present invention shows a kidney-protection effect from renal toxicity caused by an anti-cancer agent, and thus can be useful as an additive for a pharmaceutical composition for preventing, improving or treating renal toxicity, an anti-cancer adjuvant or a health functional food.

BRIEF DESCRIPTION OF DRAWINGS

FIG. 1 is a cell survival rate of canine kidney cells (MDCK) when cisplatin is added after treatment with an extracellular polysaccharide of *Ceriporia lacerata* (CL01).

BEST MODE FOR CARRYING OUT THE INVENTION

Hereinafter, the present invention is explained in detail.

In the present invention, there is provided a method for protecting a kidney, which comprises administering an extracellular polysaccharide produced by *Ceriporia lacerata*; a mycelial culture medium of *Ceriporia lacerata* containing the extracellular polysaccharide; a dried powder of the mycelial culture medium; or an extract of the mycelial culture medium, in an effective amount, to a subject in need thereof.

In the present invention, there is also provided a composition for protecting a kidney, which contains an extracellular polysaccharide produced by *Ceriporia lacerata*; a mycelial culture medium of *Ceriporia lacerata* containing the extracellular polysaccharide; a dried powder of the mycelial culture medium; or an extract of the mycelial culture medium, as an effective ingredient, and a method for protecting a kidney using the same.

As used herein, the term "extracellular polysaccharide (EPS)" refers to part of the cell wall of a microorganism such as fungi, which is a polysaccharide secreted extracellularly to form a capsule around it or a mucilage secreted around a cell or into a medium. The extracellular polysaccharide is secreted by a microorganism in order to protect itself from external environment such as antibodies, toxic materials, protozoa, bacteriophages, etc.

The extracellular polysaccharide may comprise 40 to 60 wt % sugar and 30 to 40 wt % protein, 40 to 50 wt % sugar and 32 to 38 wt % protein, 43 to 47 wt % sugar and 33 to 36 wt % protein, or about 45 wt % sugar and about 34 wt % protein.

The sugar may include mannose, galactose and glucose.

The extracellular polysaccharide may have a molecular weight of 100 to 150 kDa, 110 to 140 kDa or 115 to 125 kDa, more specifically about 120 kDa.

As used herein, the term "protecting a kidney" refers to improving a kidney function or reducing the extent of damage compared with a treatment case without administration of an effective ingredient or a composition of the present invention, by administering an effective ingredient or a composition of the present invention to a subject whose kidney is damaged or shows impaired function.

According to one embodiment of the present invention, the protection of a kidney may comprise protecting a kidney from damage or impaired function caused by anti-cancer therapy. Specifically, the protection of a kidney may be carried out by administrating an effective ingredient (an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium) to a patient whose kidney is expected to be damaged or show impaired function due to anti-cancer therapy, at the start of the anti-cancer therapy before such damage or functional impairment takes place.

The anti-cancer therapy may comprise radiotherapy or chemotherapy. Specifically, the effective ingredient of the present invention is capable of protecting a kidney from renal toxicity arising from an anti-cancer agent. The anti-cancer agent may include any anti-cancer agent which causes toxicity, for example, platinum-based anti-cancer agents, specifically cisplatin, carboplatin, oxaliplatin, and nedaplatin, etc.

According to one embodiment of the present invention, the extracellular polysaccharide may be prepared by the preparation method comprising the steps of: (a) culturing the mycelia of *Ceriporia lacerata* in a liquid to prepare mycelial culture medium of *Ceriporia lacerata*; (b) drying the mycelial culture medium of *Ceriporia lacerata* to form powders; and (c) extracting the powders of the mycelial culture medium of *Ceriporia lacerata* with a solvent, and filtering and concentrating the resultant extract under reduced pressure.

The medium for culturing in a liquid in the step (a) may contain sugar, glucose, starch, sorghum flour, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

Specifically, the medium may contain 0.2 to 3 wt % sugar, 0.2 to 3 wt % glucose, 0.2 to 4 wt % starch, 0.1 to 0.5 wt % sorghum flour, 0.1 to 0.5 wt % barley powder, 0.2 to 3 wt % soybean flour, 0.05 to 0.1 wt % magnesium sulfate (MgSO4), 0.05 to 0.25 wt % monopotassium phosphate ($KH_2PO_4$), 0.05 to 0.25 wt % dipotassium phosphate ($K_2HPO_4$) and residual quantity of water.

The culture in a liquid of the step (a) may be conducted under a blue LED light source, and may be conducted with a carbon dioxide concentration maintained at 1,000 to 2,000 ppm.

For example, the culture in a liquid may be conducted for 8 to 13 days at 20 to 28° C., under a blue LED light source, with the pH maintained at 4.5 to 6.0, an illuminance maintained at 0.1 to 0.8 LUX, an air injected at 0.5 to 2.0 kgf/cm$^2$, and carbon dioxide concentration maintained at 1,000 to 2,000 ppm. Specifically, the culture may be conducted for 5 to 15 days at 20 to 25° C., with the pH of 4.5 to 6.0, an air injected at 0.5 to 2.0 kgf/cm$^2$, and carbon dioxide concentration of 1,000 to 2,000 ppm. The above culture conditions are preferred to attain a high content of extracellular polysaccharide.

The parent strain for use in step (a) may be a strain obtained by culturing an excellent strain having been stored in PDA (potato dextrose agar) medium at 1 to 5° C. in PDB (potato dextrose broth) medium in Erlenmeyer flask using a shaking incubator at a constant temperature of 25° C. for 7 to 9 days. Also, after the parent strain is cultured, the culture medium or mycelia obtained therefrom may be used as an inoculation source. Herein, the amount of the mycelium to be inoculated is preferably about 0.5% (w/v) based on the solution to be cultured. Since a high amount of the mycelia (%/100 mL, w/v) does not necessarily result in a high content of the extracellular polysaccharide, the medium composition may be preferably selected such that it provides conditions for maximizing the content of extracellular polysaccharide, rather than the best conditions for the growth of mycelia.

The culture medium may be separated and purified into mycelia and an aqueous solution. Specifically, the separation and purification may be conducted by removing mycelia from the culture medium using a centrifuge and repeatedly purifying the remaining solution using a multi-sheet filter press and a vibrating membrane separator (PALLSEP), followed by irradiation with UV rays for 1 minute. Also, the culture medium may be sealed and stored after removing oxygen, since the presence of mycelia in the culture medium may result in the change in the content of the effective ingredient due to the growth of the mycelia.

In the step (b), the mycelial culture medium prepared in the step (a) may be dried to form a powder. In order to prevent the loss of an effective substance, the drying may be carried out at a temperature of 40° C. or lower, more specifically 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In the step (c), after the dried powders of mycelial culture medium obtained in the step (b) are extracted with a solvent, an extracellular polysaccharide, the effective ingredient according to the present invention, is isolated.

Specifically, 3 to 10 g of the dried powders of mycelial culture medium may be added to be suspended in 100 mL of distilled water, and the suspension may be centrifuged at 5,000 to 10,000 rpm for 10 to 30 minutes to obtain a supernatant. A 2- to 3-fold amount of extraction solvent may be added to the supernatant, and the solution may be placed in a refrigerator at 1 to 5° C. and allowed to stand for 10 to 15 hours. The supernatant in the solution which had been allowed to stand may be obtained and centrifuged again at 5,000 to 10,000 rpm for 10 to 30 minutes, and the precipitate may be recovered, thereby preparing crude extracellular polysaccharide. The crude extracellular polysaccharide may be vacuum freeze dried at a temperature of 30° C. or lower to obtain an extracellular polysaccharide.

The extraction solvent may be a solvent selected from the group consisting of water, lower alcohol having 1 to 4 carbon atoms, acetone, ether, chloroform and ethyl acetate, or a mixture thereof. More specifically, it may be a solvent selected from the group consisting of water, methanol, ethanol, butanol, acetone and ethyl acetate, or a mixture thereof, and more preferably, it may be water or 50 to 99% (v/v) aqueous solution of ethanol.

The composition used in the method for protecting a kidney according to the present invention may be a composition containing an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

In addition, the above composition for protecting a kidney may consist essentially of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient. Herein, the composition for protecting a kidney may further contain an excipient or an additive commonly used in drugs or supplementary food for facilitating storage without disturbing the kidney-protection effect of the composition or causing interaction.

The composition for protecting a kidney may be mixed with a pharmaceutically or sitologically acceptable excipient for the purpose of preventing, improving or treating renal toxicity, and may be administered as a pharmaceutical composition or a supplementary food. In addition, the composition for protecting a kidney may be used as an additive to a pharmaceutical composition, an anti-cancer adjuvant or health functional food, etc. Herein, the amount and usage form of the composition may be adequately adjusted according to the purpose of the usage of the composition.

The renal toxicity may be one arising from an anti-cancer agent, and the anti-cancer agent includes all anti-cancer agents which cause toxicity. For example, the anti-cancer agent that causes toxicity may be a platinum-based anti-cancer agent, which is selected from the group consisting of cisplatin, carboplatin, oxaliplatin, nedaplatin and a mixture thereof.

The extracellular polysaccharide may be comprised in an amount of 0.1 to 80 wt %, or 0.1 to 50 wt %, based on the total weight of the composition for protecting a kidney, and mycelial culture medium of *Ceriporia lacerata*, the dried powders thereof or an extract of the mycelial culture medium may be adequately comprised in an amount which corresponds to the above amount of the extracellular polysaccharide. More specifically, however, the effective content of an extracellular polysaccharide; a mycelial culture medium containing the extracellular polysaccharide; the dried powders of the mycelial culture medium; or an extract of the mycelial culture medium may be adequately adjusted according to the method of use and purpose of the composition.

In addition, the present invention also provides a pharmaceutical composition for preventing and treating renal toxicity which comprises the composition for protecting a kidney described above.

The pharmaceutical composition may comprise a suitable carrier, an excipient and a diluent which are conventionally used, together with an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

A pharmaceutical composition according to the present invention can be formulated and used in accordance with a conventional method. Suitable formulations may include, but are not limited to, tablets, pills, powders, granules, sugar-coated tablets, hard or soft capsules, solutions, suspensions or emulsions, injections, suppositories and the like.

A pharmaceutical composition according to the present invention can be prepared into a suitable formulation using a pharmaceutically inert organic or inorganic carrier. That is, if the formulation is a tablet, a coated tablet, a sugar-coated tablet or a hard capsule, it may comprise lactose, sucrose, starch or a derivative thereof, talc, calcium carbonate, gelatin, or stearic acid or a salt thereof. Also, if the formulation is a soft capsule, it may comprise vegetable oil, wax, fat, or semi-solid or liquid polyol. Furthermore, if the formulation is in the form of a solution or syrup, it may comprise water, polyol, glycerol, vegetable oil, and the like.

A pharmaceutical composition according to the present invention may further comprise a preservative, a stabilizer, a humectant, an emulsifier, a solubilizer, a sweetener, a coloring agent, an osmotic pressure regulator, an antioxidant and the like in addition to the above carrier.

A method of administering a pharmaceutical composition according to the present invention can be easily selected in accordance with the formulation, which may be oral or parenteral administration. The dosage may vary depending on the patient's age, sex, weight, disease severity, and/or route of administration, but is generally 5 to 1,000 mg/kg (body weight) and specifically 10 to 600 mg/kg (body weight) based on the extracellular polysaccharide as, an effective ingredient, which may be administered once to three times per day. However, such dosage does not limit the scope of the present invention.

A pharmaceutical composition according to the present invention not only provides an excellent kidney-protection effect but also shows little toxicity and adverse events, and thus can safely be used for the purpose of kidney-protection by long-term administration.

In addition, the method for protecting a kidney may comprise administering the composition for protecting a kidney in combination with anti-cancer therapy as an anti-cancer adjuvant. Specifically, the method for protecting a kidney may comprise administering the composition for protecting a kidney as an anti-cancer adjuvant to a patient undergoing anti-cancer therapy.

The anti-cancer adjuvant may be administered alone before or after the administration of an anti-cancer agent, or may be mixed with the anti-cancer agent and administered together as an anti-cancer composition. When a composition for protecting a kidney according to the present invention is administered as an anti-cancer adjuvant along with an anti-cancer agent, it may be comprised in a suitable ratio with the anti-cancer agent depending on the condition of the patient, dosage and administration period of the anti-cancer agent, and the like. The amount of the anti-cancer adjuvant may be 0.01 to 10 times the total weight of the anti-cancer agent.

The anti-cancer agent may be a platinum-based anti-cancer agent, specifically cisplatin, carboplatin, oxaliplatin, nedaplatin, and the like.

Furthermore, the present invention provides a health functional food for preventing or improving renal toxicity comprising the composition for protecting a kidney described above.

Health functional food according to the present invention may be in the form of powders, granules, a tablet, a capsule or a drink, and may be a candy, a chocolate, a gum, a tea, a vitamin complex, a health supplementary food, and the like.

Herein, an extracellular polysaccharide; a mycelial culture medium containing the extracellular polysaccharide; dried powders of the mycelial culture medium; or an extract of the mycelial culture medium of the present invention may be conventionally comprised in an amount of 0.01 to 50 wt %, or 0.1 to 20 wt % based on the total food weight; and in the case of a health drink composition, in an amount of 0.02 to 10 g, or 0.3 to 1 g based on 100 mL of the health drink composition.

The food may further comprise a sitologically acceptable food supplementary additive in addition to an extracellular polysaccharide of Ceriporia lacerates, a mycelial culture medium containing the extracellular polysaccharide; dried powders of the mycelial culture medium; or an extract of the mycelial culture medium.

Hereinafter, the present invention will be described in more detail with the following Examples. The following Examples are provided to illustrate the present invention, but the scope of the present invention is not limited thereto.

Preparation Example 1. Preparation of Culture Medium of Ceriporia lacerata

Ceriporia lacerata mycelia isolated from Quercus serrata collected at Sangju city, Gyeongbuk province were subcultured to obtain a parent strain which was subsequently freeze-stored at −80° C. The freeze-stored strain was cultured with 2-3 passages in PDA (potato dextrose agar) medium (87 plastic bulbs; Difco, Becton Dickinson and Company), and the strain (hereinafter referred to as "PDA culture strain") was stored in a refrigerator at 4° C. until use. Then, 600 mL of the PDB (potato dextrose broth) medium (Difco, Becton Dickinson and Company) was placed in an Erlenmeyer flask, and then the PDA culture strain was added thereto and shake-cultured for 8 days to obtain a PDB culture strain.

On the other hand, in order to culture the strain, a liquid culture medium containing 1.5 wt % sugar, 0.5 wt % glucose, 0.5 wt % potato starch, 0.25 wt % sorghum flour, 0.25 wt % barley powder, 0.75 wt % soybean flour, 0.05 wt % magnesium sulfate ($MgSO_4$), 0.05 wt % monopotassium phosphate ($KH_2PO_4$), 0.05 wt % dipotassium phosphate ($K_2HPO_4$) and residual quantity of water was sterilized for 20 minutes in a 800 L fermenter at 121° C., with the air injected at 1.5 kgf/cm², Then, the medium was cooled to 23° C., and inoculated with 600 mL of the PDB culture strain used as a starter, and Ceriporia lacerata mycelia were liquid-cultured in the medium for 10 days at a constant temperature of 23° C., under a blue LED light source, with the air injected at 0.5 to 1.5 kgf/cm², an illuminance maintained at 0.5 LUX, and a carbon dioxide concentration of 2,000 ppm, to prepare the mycelial culture medium of Ceriporia lacerata.

Preparation Example 2. Preparation of Dried Powders of Culture Medium of Ceriporia lacerata The mycelial culture medium of Ceriporia lacerata prepared in the Preparation Example 1 was vacuum-freeze-dried by a vacuum freeze dryer at 25° C. for 72 hours to form powders, thereby preparing the dried powders of mycelial culture medium of Ceriporia lacerata.

Preparation Example 3. Preparation of Extract of Culture Medium of Ceriporia lacerata 5 g of the dried powders of the mycelial culture medium of Ceriporia lacerata prepared in Preparation Example 2 was added to 100 mL of distilled water and sufficiently suspended, and then the resulting solution was centrifuged at 8,000 rpm for 20 minutes. Then the supernatant separated therefrom was mixed with a 2- to 3-fold amount of ethanol and allowed to stand at 4° C. for 12 hours. Thereafter, the resultant supernatant was taken and an extract of the mycelial culture medium of Ceriporia lacerata was obtained therefrom.

Preparation Example 4. Preparation of Extracellular Polysaccharide (Hereinafter Referred to as "EPS") from Culture Medium of Ceriporia lacerata The extract of the mycelial culture medium of Ceriporia lacerata obtained in Preparation Example 3 was further centrifuged at 8,000 rpm for 20 minutes. Thereafter, the precipitate was recovered to obtain crude EPS. The crude EPS was vacuum freeze dried in a vacuum freeze dryer at 25° C. for 72 hours to obtain an EPS produced by Ceriporia lacerata.

Example 1. Evaluation of Property of EPS 1.1. Molecular Weight Measurement of EPS Using Gel Permeation Chromatography (GPC)

The EPS prepared in Preparation Example 4 was dissolved in a solution of 0.1 M $Na_2SO_4$/0.05 M $NaN_3$ (adjusted to pH 4 with glacial acetic acid) to a concentration of 1% (w/v), and then the mixture was centrifuged at 4,000 rpm for 0.5 hour, then the supernatant was isolated and filtered with a 0.45 μm syringe filter and analyzed by GPC.

The refractive index of the detector was used for the GPC analysis; OHpak SB 805 HQ (Shodex, Japan) was used for the GPC column; and 0.1 M $Na_2SO_4$/0.05 M $NaN_3$ (adjusted to pH 4 with glacial acetic acid) was used for a mobile phase. And the mobile phase was allowed to flow at a flow rate of 0.1 mL/min. Standard curves were generated using dextrans (American Polymer Corporation, USA) with different molecular weights (130 kDa, 400 kDa, 770 kDa or 1,200 kDa). The molecular weight of EPS was measured using refractive index (RI) measuring instrument Knauer K-2310 (Germany). The measurement conditions are summarized in Table 1 below.

TABLE 1

| | Measurement of molecular weight |
|---|---|
| GPC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 0.1 mL/min |
| Measuring instrument | RI (Knauer K-2310) |

As a result, the molecular weight of EPS of the Preparation Example 4 was about 120 kDa.

1.2. Measurement of Sugar and Protein Contents of EPS

The EPS prepared in Preparation Example 4 was subjected to secondary purification and treated with a protein-hydrolysis enzyme to measure sugar and protein contents.

Specifically, the primary-purified EPS (EPS prepared in Preparation Example 4) was dissolved in distilled water and centrifuged at 8,000 rpm for 20 minutes to separate the supernatant. A 2- to 3-fold amount of ethanol was added thereto, and the mixture was placed and allowed to stand in a refrigerator at 4° C. for 12 hours. Thereafter, the resultant supernatant was taken and centrifuged again at 8,000 rpm for 20 minutes, and the precipitate was recovered to obtain a secondary-purified EPS. The secondary-purified EPS was dissolved in distilled water and treated with Alcalase, a protein-hydrolysis enzyme, at a concentration of 0.5% (w/v) at 50° C. for 30 minutes.

The sugar content was measured by the phenol-sulfuric acid method. Specifically, 25 μL of 80% (w/v) phenol was added to 1 mL of each of the samples diluted at various concentrations, and then 2.5 mL of sulfuric acid was added thereto and the mixture was cooled to room temperature. The sugar content was calculated by measuring the absorbance at a wavelength of 465 nm.

Also, the protein content was measured by BCA method (Smith P K et al., *Analytical Biochemistry*, 150 (1): 76-85, 1985) and bovine serum albumin was used as a standard.

The sugar and protein contents measured as described above are shown in Table 2 below. The sugar content of EPS was 45 to 51 wt % and the protein content was 33 to 34 wt %.

TABLE 2

| | Yield (%) | Total sugar content (%) | Total protein content (%) |
|---|---|---|---|
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: Alkalase 0.5%, 50° C., 30 minutes.
Each value represents mean ± SE (n ≥ 3).

As a result of analyzing sugar composition of EPS of Preparation Example 4, it was found that EPS mainly contains mannose, galactose and glucose.

Example 2. Confirmation of Kidney-Protection Effect

MTT analysis was conducted to confirm the kidney-protection effect of the EPS prepared in Preparation Example 4 against renal toxicity caused by an anti-cancer agent.

First, MDCK cell line (Korean Cell Line Bank, Korea) was cultured in DMEM medium supplemented with 10% fetal bovine serum, 100 μg/mL streptomycin and 100 U/mL penicillin at 37° C. and 5% $CO_2$. 100 μL each of the cultured cells was dispensed to 96-well plate at $2 \times 10^4$ cells/mL, and cultured for 24 hours. The EPS was added thereto to a concentration of 25, 50 or 250 μg/mL, and 2 hours thereafter, 5 μM of cisplatin was added thereto.

24 hours after cisplatin was added, 10 μL of MTT (1 mg/mL) dissolved in PBS was added to each well, subjected to reaction for 4 hours. After 4 hours, the formation of formazan was confirmed, and the supernatant was completely removed so that formazan may not be dispersed. Then, the resultant was added to dissolve, in 100 μL of DMSO and dissolved, followed by the measurement of the absorbance at 570 nm using ELISA reader.

The results are shown in FIG. 1 as relative values when the value of the negative control group treated with neither cisplatin nor EPS was set at 100%.

As a result, as shown in FIG. 1, the survival rate of MDCK cell line was about 60% when treated with cisplatin only, but the MDCK cell line death was inhibited in a concentration-dependent manner when treated with EPS. The cell survival rate was increased up to about 80% when EPS was added to the concentration of 250 μg/mL.

These results indicates that not only an EPS according to the present invention, but also a mycelial culture medium of *Ceriporia lacerata* containing the EPS, dried powders of the mycelial culture medium, or an extract of the mycelial culture medium shows the kidney-protection effect from renal toxicity caused by an anti-cancer agent.

The invention claimed is:

1. A method for protecting a kidney, which comprises administering an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, in an effective amount, to a subject in need of protecting a kidney.

2. The method of claim 1, wherein the extracellular polysaccharide comprises 40 to 60 wt % sugar and 30 to 40 wt % protein, and has a molecular weight of 100 to 150 kDa.

3. The method of claim 2, wherein the extracellular polysaccharide comprises 43 to 47 wt % sugar and 33 to 36 wt % protein, and has a molecular weight of 115 to 125 kDa.

4. The method of claim 2, wherein the sugar contains mannose, galactose and glucose.

5. The method of claim 1, wherein the extracellular polysaccharide is prepared by the preparation method comprising the steps of:
   (a) culturing the mycelia of *Ceriporia lacerata* in a liquid to prepare a mycelial culture medium of *Ceriporia lacerata*;
   (b) drying the mycelial culture medium of *Ceriporia lacerata* to form powders; and
   (c) extracting the powders of the mycelial culture medium of *Ceriporia lacerata* with a solvent, and filtering and concentrating the resultant extract under reduced pressure.

6. The method of claim 5, wherein the medium for culturing in a liquid comprises sugar, glucose, starch, sorghum flour, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium is 4.5 to 6.0.

7. The method of claim 5, wherein the culturing in a liquid is conducted under a blue LED light source.

8. The method of claim 5, wherein the culturing in a liquid is conducted with a carbon dioxide concentration at 1,000 to 2,000 ppm.

9. The method of claim 1, wherein the subject in need of protecting a kidney is a patient whose kidney is damaged or shows impaired function due to anti-cancer therapy.

10. The method of claim 9, wherein the anti-cancer therapy is anti-cancer agent therapy.

11. The method of claim 10, wherein the anti-cancer agent is a platinum-based anti-cancer agent.

12. The method of claim 11, wherein the platinum-based anti-cancer agent is selected from the group consisting of cisplatin, carboplatin, oxaliplatin, nedaplatin and a mixture thereof.

13. The method of claim 1, wherein the extracellular polysaccharide produced by *Ceriporia lacerata*; the mycelial culture medium of *Ceriporia lacerata* containing the extracellular polysaccharide; the dried powders of the mycelial culture medium; or the extract of the mycelial culture medium is administered in the form of a pharmaceutical composition which further contains a pharmaceutically acceptable excipient.

14. The method of claim 1, wherein the extracellular polysaccharide produced by *Ceriporia lacerata*; the mycelial culture medium of *Ceriporia lacerata* containing the extracellular polysaccharide; the dried powders of the mycelial culture medium; or the extract of the mycelial culture medium is administered in the form of a health functional food which further contains a sitologically acceptable excipient.

15. The method of claim 9, wherein the extracellular polysaccharide produced by *Ceriporia lacerata*; the mycelial culture medium of *Ceriporia lacerata* containing the extracellular polysaccharide; the dried powders of the mycelial culture medium; or the extract of the mycelial culture medium is administered in the form of a pharmaceutical composition which further contains a pharmaceutically acceptable excipient.

16. The method of claim 1, wherein the subject in need of protecting a kidney is a patient receiving anti-cancer therapy, and the extracellular polysaccharide produced by *Ceriporia lacerata*; the mycelial culture medium of *Ceriporia lacerata* containing the extracellular polysaccharide; the dried powders of the mycelial culture medium; or the extract of the mycelial culture medium is administered to the patient in combination with the anti-cancer therapy.

* * * * *